United States Patent [19]
Sullivan et al.

[11] Patent Number: 5,989,549
[45] Date of Patent: Nov. 23, 1999

[54] ACROSOMAL SPERM PROTEIN AND USES THEREOF

[75] Inventors: Robert Sullivan; Bruno Bérubé; Christine Légaré; Christian Gaudreault, all of Québec, Canada

[73] Assignee: Immucon Inc., Montréal, Canada

[21] Appl. No.: 09/090,567

[22] Filed: Jun. 8, 1998

[51] Int. Cl.⁶ .................................................. A61K 39/00
[52] U.S. Cl. .................................. 424/184.1; 424/185.1; 530/806; 530/852
[58] Field of Search .............................. 424/184.1, 185.1; 530/806, 852

[56] References Cited

U.S. PATENT DOCUMENTS 5,723,305   3/1998   Sullivan et al. .................... 435/7.21

OTHER PUBLICATIONS

Bérubé, B. et al., *Biol. Reprod.* 51: 1255–1263, 1994;.

Boué, F. et al., *Biol. Reprod.*, 51; 577–587, 1994;.

Boué, F. et al., *Biol. Reprod.*, 54: 1018–1024, 1996;.

Boué, F., et al, *Biol. Reprod.*, 54: 1009–1017, 1996.

*Primary Examiner*—David Saunders
*Attorney, Agent, or Firm*—Swabey Ogilvy Renault; France Côté

[57] ABSTRACT

The present invention relates to the use of acrosomal sperm protein in immunocontraception of male and female subjects and uses thereof as a marker for fertility.

3 Claims, 9 Drawing Sheets

N-TERMINAL

| | | | | | | | | | | | | | | |
|---|---|---|---|---|---|---|---|---|---|---|---|---|---|---|
| P26h | MK | LN | FS | XL | RA | LV | TG | AG | KG | IG | IG | XD | TA | KA | L |
| Adipsin | -- | -- | -- | G- | -- | -- | -- | -- | -- | -- | -- | R- | -V | -- | - |

NCS FRAGMENT

| | | | | | | | | | | | | | |
|---|---|---|---|---|---|---|---|---|---|---|---|---|---|
| P26h | XA | TE | KA | LG | XI | GP | VX | XL | VN | NA | AL | XX | XQ |
| Adipsin | D- | -- | -- | -- | G- | -- | -D | L- | -- | -- | -- | VM | I- |

CNBr fragment

| | | | | | |
|---|---|---|---|---|---|
| P26h | LY | PY | KX | RV | N |
| Adipsin | -G | -H | -I | -- | - |

Fig. 1

```
GTCCCTGGAGGTTGGCTGTAGGATTCAGGTGGCTTGCTCAGGCTGGG         47
ATCAAGGACACAGTGAGCAGATCAACCTTAACCTCAGCCCCTCCC           92
CTCGCCACAGGAGGACACTGGTGTCAGCAGC ATG AAG CTG AAT        135
                                 M   K   L   N          4

TTC ACT GGT CTC AGG GCT CTG GTG ACC GGG GCA GGG AGA GGG 177
 F   T   G   L   R   A   L   V   T   G   A   G   R   G  18

ATT GGG CGA GGC ACT GCG AAA GCC CTG CAT GCC TCA GGA GCC 219
 I   G   R   G   T   A   K   A   L   H   A   S   G   A  32

AAA GTG GTG GCC GTG TCA CTC ATC AAC GAA GAC CTG GTC AGC 261
 K   V   V   A   V   S   L   I   N   E   D   L   V   S  46

CTG GCC AAA GAG TGT CCG GGC ATA GAG CCT GTG TGT GTG GAC 303
 L   A   K   E   C   P   G   I   E   P   V   C   V   D  60

CTG GGT GAC TGG GAG GCC ACA GAG AAG GCA CTG GGC CGT ATT 345
 L   G   D   W   E   A   T   E   K   A   L   G   R   I  74

GGC CCC GTG GAC CTG CTG GTG AAC AAT GCG GCG GTG GCG CTA 387
 G   P   V   D   L   L   V   N   N   A   A   V   A   L  88

GTG CAG CCT TTC ATA CAG TCT ACC AAG GAG GTC TTT GAC AGG 429
 V   Q   P   F   I   Q   S   T   K   E   V   F   D   R 102

TCC TTC AAT GTG AAT GTG CGC TCT GTG CTG CAA GTG TCC CAG 471
 S   F   N   V   N   V   R   S   V   L   Q   V   S   Q 116

ATG GTA GCC AAG GGC ATG ATT AAC CGT GGA GTG GCA GGA TCC 513
 M   V   A   K   G   M   I   N   R   G   V   A   G   S 130

ATT GTC AAC ATC TCC AGC ATG GTG GCC TAT GTC ACC TTC CCT 555
 I   V   N   I   S   S   M   V   A   Y   V   T   F   P 144

GGT CTG GCC ACG TAC AGC TCC ACC AAG GGT GCT ATA ACC ATG 597
 G   L   A   T   Y   S   S   T   K   G   A   I   T   M 158

CTG ACC AAA GCC ATG GCC ATG GAG CTG GGA CCA TAC AAG ATC 639
 L   T   K   A   M   A   M   E   L   G   P   Y   K   I 172

CGG GTG AAC TCT GTA AAC CCT ACC GTG GTG CTG ACT GAC ATG 681
 R   V   N   S   V   N   P   T   V   V   L   T   D   M 186

GGC AAG AAA GTC TCT GCA GAC CCG GAA TTT GCC AAG AAG CTC 723
 G   K   K   V   S   A   D   P   E   F   A   K   K   L 200

AAG GAG CGC CAC CCA CTG AGG AAG TTC GCA GAG GTG GAG GAC 765
 K   E   R   H   P   L   R   K   F   A   E   V   E   D 214
```

Fig. 3A

```
GTG GTC AAC AGC ATC CTC TTC CTG CTC AGC GAC AGC AGC GCC   807
 V   V   N   S   I   L   F   L   L   S   D   S   S   A   228

TCT ACC AGC GGC TCT GGC ATC CTG GTG GAC GCT GGT TAC CTG   849
 S   T   S   G   S   G   I   L   V   D   A   G   Y   L   242

GCC TCC TAG     ACGGCCCAGGTGCAGGGGACTCCTGGAGACTTCC        892
 A   S  Amber                                             244

CTGGCCTCACCCTTACATCAAGACCCCGCCTTCAACCCAACCCAATAAT         941
TTTGTTCGAATCCTGTAGAGCCCCACCCCACACACATCCATCCCCAACT         990
TTAGACTCCGGGATCCCGCCATTCCATACCAGCTATGCTGAGATAATT         1038
TGATTAAATAAGTATCCCAAACCACAAAAAAAAAAAAAAAAA              1081
```

Fig. 3B

```
P26h         MK LN FT GL RA LV TG AG RG IG RG TA KA LH AS GA KV VA VS LI NE DL VS LA KE  50
Adipsin      -- -- -- -S -- -- -- -- -- -- -- -- -D -V -- -- -- -- -T RT -S -- -- -- --  50
C.Reductase  -Q M- -S -- -- -- -- -- -K- -- -- -- -D -V -- -- -R- -- -T RT -G -- -- S Q-  50

P26h         CP GI EP VC VD LG DWEA TE KA LG RI GP VD LL VN NA AV AL VQ PF IQ ST KE VF 100
Adipsin      -- -- -- -- -- -- -- -D -- -- -- -G -- -- -- -- -- -- -L VI M- -- LE V- -A- 100
C.Reductase  -- -- -- -- -- -- -- -- -- -- -R -- -- GV -- -- -- -- -- M- -- LD T- -- -- 100

P26h         DR SF NV NV RS VL QV SQ MV AK GMIN RG VA GS IV NI SS MVAY YT FP GL AT YS 150
Adipsin      -- -- -S- -L -- -- -F -- -- -- -R D- -- -P -- -- -V -- -- -- -H -- -- -- 150
C.Reductase  -- -- -- -L -- -F -- -- -- -- -L- -R S- -E -- -P -- -- -V -- -- SH -- Y- -A- 150

P26h         ST KG AI TM LT KA MAME LG PY KI RV NS VN PT VV LT DMGK KV SA DP EF AK KL 200
Adipsin      -- -- -M -- -- -- -- -- -- -- -H -- -- -- -- -- -- -- -- -- -- -- -R -- 200
C.Reductase  -- -- -M -- -- -- -S -- -- -- -H -- -- -- -- -A- -R S- TS -- -L -R -- 200

P26h         KE RH PL RK FA EV ED VV NS IL FL LS DS SA ST SG SG I L VD AG YL AS 244
Adipsin      -- -- -- -- -- -- -- -- -- -- -- -- -R -- -- -- -- -- G- -- -- -- 244
C.Reductase  -- -- -M -- -- -- -- -- -- -- -- -- -R -- -- -- -- -S -F -- -- -- 244
```

Fig. 4

```
MKLNFTGLRALVTGAGRGIGRGTAKALHASGAKVVAVSLINEDLVSLAKECPGIEPVCVDLGDWEATEKALGRIGPVDLL
 ::  : ::::::::: :::: ::  ::::::  :::::::  : ::::::::::::::::::::: ::::: :::::
MELFLAGRRVLVTGAGKGIGRGTVQALHATGARVVAVSRTQADLDSLVRECPGIEPVCVDLGDWEATERALGSVGPVDLL
|————————|————————|————————|————————|————————|————————|————————|————————|
10       20       30       40       50       60       70       80

VNNAAVALVQPFIQSTKEVFDRSFNVNVRSVLQVSQMVAKGMINRGVAGSIVNISSMVAYVTFPGLATYSSTKGAITMLT
:::::::::: ::: :: ::::::::: ::::::::  :  :::::::::::::: :::::::::::: ::::: :::
VNNAAVALLQPFLEVTKEAFDRSFEVNLRAVIQVSQITVARGLIARGVPGAIVNVSSQCSQRAVINHSVYCSTKGALDMLT
|————————|————————|————————|————————|————————|————————|————————|————————|
90       100      110      120      130      140      150      160

KAMAMELGPYKIRVNSVNPTVVLTDMGKKVSADPEFAKKLKERHPLRKFAEVEDVVNSILFLLSDSSASTSGSGILVDAG
:: :::::: ::::: :::::: : : :::::       :    :: :: :: :                      ·
KVMALELGPHKIRVNAVNPTVVMTSMASPPGVTPTSQDYAEPNPTMQVC·
|————————|————————|————————|————————|————————|————————|————————|————————|
170      180      190      200      210      220      230      240
```

Fig. 8

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 1081 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: Coding Sequence
      (B) LOCATION: 124...853
      (D) OTHER INFORMATION:

(xi) SEQUENCE DESCRIPTION: SEQ ID NO:1:

```
GTCCCTGGAG GTTGGCTGTA GGATTCAGGT GGCTTGCTCA GGCTGGGATC AAGGACACAG        60

TGAGCAGATC AACCTTAACC TCAGCCCCTC CCCTCGCCAC AGGAGGACAC TGGTGTCAGC       120

AGC ATG AAG CTG AAT TTC ACT GGT CTC AGG GCT CTG GTG ACC GGG GCA        168
    Met Lys Leu Asn Phe Thr Gly Leu Arg Ala Leu Val Thr Gly Ala
    1               5                   10                  15

GGG AGA GGG ATT GGG CGA GGC ACT GCG AAA GCC CTG CAT GCC TCA GGA        216
Gly Arg Gly Ile Gly Arg Gly Thr Ala Lys Ala Leu His Ala Ser Gly
                20                  25                  30

GCC AAA GTG GTG GCC GTG TCA CTC ATC AAC GAA GAC CTG GTC AGC CTG        264
Ala Lys Val Val Ala Val Ser Leu Ile Asn Glu Asp Leu Val Ser Leu
            35                  40                  45
```

```
GCC AAA GAG TGT CCG GGC ATA GAG CCT GTG TGT GTG GAC CTG GGT GAC         312
Ala Lys Glu Cys Pro Gly Ile Glu Pro Val Cys Val Asp Leu Gly Asp
        50                  55                  60

TGG GAG GCC ACA GAG AAG GCA CTG GGC CGT ATT GGC CCC GTG GAC CTG         360
Trp Glu Ala Thr Glu Lys Ala Leu Gly Arg Ile Gly Pro Val Asp Leu
65                  70                  75

CTG GTG AAC AAT GCG GCG GTG GCG CTA GTG CAG CCT TTC ATA CAG TCT         408
Leu Val Asn Asn Ala Ala Val Ala Leu Val Gln Pro Phe Ile Gln Ser
80                  85                  90                  95

ACC AAG GAG GTC TTT GAC AGG TCC TTC AAT GTG AAT GTG CGC TCT GTG         456
Thr Lys Glu Val Phe Asp Arg Ser Phe Asn Val Asn Val Arg Ser Val
                100                 105                 110

CTG CAA GTG TCC CAG ATG GTA GCC AAG GGC ATG ATT AAC CGT GGA GTG         504
Leu Gln Val Ser Gln Met Val Ala Lys Gly Met Ile Asn Arg Gly Val
            115                 120                 125

GCA GGA TCC ATT GTC AAC ATC TCC AGC ATG GTG GCC TAT GTC ACC TTC         552
Ala Gly Ser Ile Val Asn Ile Ser Ser Met Val Ala Tyr Val Thr Phe
        130                 135                 140

CCT GGT CTG GCC ACG TAC AGC TCC ACC AAG GGT GCT ATA ACC ATG CTG         600
Pro Gly Leu Ala Thr Tyr Ser Ser Thr Lys Gly Ala Ile Thr Met Leu
    145                 150                 155

ACC AAA GCC ATG GCC ATG GAG CTG GGA CCA TAC AAG ATC CGG GTG AAC         648
Thr Lys Ala Met Ala Met Glu Leu Gly Pro Tyr Lys Ile Arg Val Asn
160                 165                 170                 175

TCT GTA AAC CCT ACC GTG GTG CTG ACT GAC ATG GGC AAG AAA GTC TCT         696
Ser Val Asn Pro Thr Val Val Leu Thr Asp Met Gly Lys Lys Val Ser
                180                 185                 190

GCA GAC CCG GAA TTT GCC AAG AAG CTC AAG GAG CGC CAC CCA CTG AGG         744
Ala Asp Pro Glu Phe Ala Lys Lys Leu Lys Glu Arg His Pro Leu Arg
            195                 200                 205

AAG TTC GCA GAG GTG GAG GAC GTG GTC AAC AGC ATC CTC TTC CTG CTC         792
Lys Phe Ala Glu Val Glu Asp Val Val Asn Ser Ile Leu Phe Leu Leu
        210                 215                 220

AGC GAC AGC AGC GCC TCT ACC AGC GGC TCT GGC ATC CTG GTG GAC GCT         840
Ser Asp Ser Ser Ala Ser Thr Ser Gly Ser Gly Ile Leu Val Asp Ala
    225                 230                 235

GGT TAC CTG GCC T CCTAGACGGC CCAGGTGCAG GGGACTCCTG AGACTTCCC            893
Gly Tyr Leu Ala Ser
240

TGGCCTCACC CTTACATCAA GACCCCGCCT TCAACCCAAC CCAATAATTT TGTTCGAATC       953

CTGTAGAGCC CCACCCCACA CACATCCATC CCCAACTTTA GACTCCGGGA TCCCGCCATT      1013

CCATACCAGC TATGCTGAGA TAATTTGATT AAATAAGTAT CCCAAACCAC AAAAAAAAAA      1073

AAAAAAAA                                                              1081

(2) INFORMATION FOR SEQ ID NO:2:

(i) SEQUENCE CHARACTERISTICS:
        (A) LENGTH: 244 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:2:

Met Lys Leu Asn Phe Thr Gly Leu Arg Ala Leu Val Thr Gly Ala Gly
1               5                   10                  15
```

```
Arg Gly Ile Gly Arg Gly Thr Ala Lys Ala Leu His Ala Ser Gly Ala
            20                  25                  30

Lys Val Ala Val Ser Leu Ile Asn Glu Asp Leu Val Ser Leu Ala
        35                  40                  45

Lys Glu Cys Pro Gly Ile Glu Pro Val Cys Val Asp Leu Gly Asp Trp
 50                  55                  60

Glu Ala Thr Glu Lys Ala Leu Gly Arg Ile Gly Pro Val Asp Leu Leu
 65                  70                  75                  80

Val Asn Asn Ala Ala Val Ala Leu Val Gln Pro Phe Ile Gln Ser Thr
                85                  90                  95

Lys Glu Val Phe Asp Arg Ser Phe Asn Val Asn Val Arg Ser Val Leu
                100                 105                 110

Gln Val Ser Gln Met Val Ala Lys Gly Met Ile Asn Arg Gly Val Ala
                115                 120                 125

Gly Ser Ile Val Asn Ile Ser Ser Met Val Ala Tyr Val Thr Phe Pro
            130                 135                 140

Gly Leu Ala Thr Tyr Ser Ser Thr Lys Gly Ala Ile Thr Met Leu Thr
145                 150                 155                 160

Lys Ala Met Ala Met Glu Leu Gly Pro Tyr Lys Ile Arg Val Asn Ser
                165                 170                 175

Val Asn Pro Thr Val Val Leu Thr Asp Met Gly Lys Lys Val Ser Ala
            180                 185                 190

Asp Pro Glu Phe Ala Lys Lys Leu Lys Glu Arg His Pro Leu Arg Lys
            195                 200                 205

Phe Ala Glu Val Glu Asp Val Val Asn Ser Ile Leu Phe Leu Leu Ser
 210                 215                 220

Asp Ser Ser Ala Ser Thr Ser Gly Ser Gly Ile Leu Val Asp Ala Gly
225                 230                 235                 240

Tyr Leu Ala Ser (2) INFORMATION FOR SEQ ID NO:3:

(i) SEQUENCE CHARACTERISTICS:
        (A) LENGTH: 912 base pairs
        (B) TYPE: nucleic acid
        (C) STRANDEDNESS: single
        (D) TOPOLOGY: linear (ii) MOLECULE TYPE: cDNA (ix) FEATURE:

(xi) SEQUENCE DESCRIPTION: SEQ ID NO:3:

GACAAAAGCT GGAGCTCCAC CGCGGTGGCG GCCGCTCTAG AACTAGTGGA TCCCCCGGGC      60

TGCAGGAATT CGGCACGAGC CGACATGGAG CTGTTCCTCG CGGGCCGCCG GGTGCTGGTC     120

ACCGGGGCAG GCAAAGGTAT AGGGCGCGGC ACGGTCCAGG CGCTGCACGC GACGGGCGCG     180

CGGGTGGTGG CTGTGAGCCG GACTCAGGCG GATCTTGACA GCCTTGTCCG CGAGTGCCCG     240

GGGATAGAAC CCGTGTGCGT GGACCTGGGT GACTGGGAGG CCACCGAGCG GGCGCTGGGC     300

AGCGTGGGCC CCGTGGACCT GCTGGTGAAC AACGCCGCTG TCGCCCTGCT GCAGCCCTTC     360

CTGGAGGTCA CCAAGGAGGC CTTTGACAGA TCCTTTGAGG TGAACCTGCG TGCGGTCATC     420

CAGGTGTCGC AGATTGTGGC CAGGGGCTTA ATAGCCCGGG GAGTACCAGG GGCCATCGTG     480

AATGTCTCCA GCCAGTGCTC CCAGCGGGCA GTAACTAACC ATAGCGTCTA CTGCTCCACC     540

AAGGGTGCCC TGGACATGCT GACCAAGGTG ATGGCCCTAG AGCTCGGGCC CCACAAGATC     600

CGAGTGAATG CAGTAAACCC CACAGTGGTG ATGACGTCCA TGGCCAGCCC ACCTGGAGTG     660
```

```
ACCCCCACAA GCCAAGACTA TGCTGAACCG AATCCCACTT GGCAAGTTTG CTGAGGTAGA      720

GCACGTGGTG AACGCCATCC TCTTTCTGCT GAGTGACCGA AGTGGCATGA CCACGGGTTC      780

CACTTTGCCG GTGGAAGGGG GCTTCTGGGC CTGCTGAGCT CCCTCCACAC ACCTCAAGCC      840

CCATGCCGTG CTCATCCTAC CCCCAATCCC TCCAATAAAC CTGATTCTGC TCCCAAAAAA      900

AAAAAAAAAA AA                                                         912

(2) INFORMATION FOR SEQ ID NO:4:

(i) SEQUENCE CHARACTERISTICS:
         (A) LENGTH: 11 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:4:

Met Glu Leu Phe Leu Ala Gly Arg Arg Val Cys
 1               5                  10

(2) INFORMATION FOR SEQ ID NO:5:

(i) SEQUENCE CHARACTERISTICS:
         (A) LENGTH: 14 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:5:

Cys Ser Gln Asp Tyr Ala Glu Pro Asn Pro Thr Trp Gln Val
 1               5                  10
```

ACROSOMAL SPERM PROTEIN AND USES THEREOF

BACKGROUND OF THE INVENTION (a) Field of the Invention

The invention relates to the use of acrosomal sperm protein in immunocontraception of male and female subjects and uses thereof as a marker for fertility.

(b) Description of Prior Art

Fertilization is a highly orchestrated process that culminates in the activation of an oocyte by a spermatozoon. Although testicular spermatozoa are fully differentiated cells, they cannot efficiently encounter the oocyte's investments. In order to acquire this property, spermatozoa must undergo post-testicular modifications within the epididymis. During this transit, the male gamete is subjected to major surface modifications such as changes in the lipids composition, acquisition of new epididymal proteins as well as post-translational modifications of sperm proteins. Taken together, these modifications are prerequisites for the spermatozoon to acquire its fertilizing ability. These processes are regulated by the epididymal luminal microenvironment which is influenced by both epididymal and testicular protein synthesis and secretion.

Using the hamster as a model, we have previously described a 26 kDa protein, the P26h, which shows immunocontraceptive properties when used to actively immunize male hamsters (Bérubé, B., Sullivan, R., 1994, Biol. Reprod., 51: 1255–1263). This protein is localized on the sperm acrosome and is acquired during the epididymal transit. P26h plays a role in egg sperm interactions as shown by the ability of P26h antibodies to inhibit sperm-zona pellucida binding in vivo and in vitro (Bérubé, B., Sullivan, R., 1994, Biol. Reprod., 51: 1255–1263).

It would be highly desirable to be provided with to the use of an acrosomal sperm protein in immunocontraception of male and female subjects.

It would be highly desirable to be provided with to the use of an acrosomal sperm protein as a marker for fertility.

SUMMARY OF THE INVENTION

One aim of the present invention is to provide the use of acrosomal sperm protein in immunocontraception of male and female subjects.

In accordance with the present invention there is provided a method of immunocontraception of a male or female subject, which comprises administering to said male or female subject an antigenic amount of P34 or an antigenic fragment thereof to elicit an immunocontraception response by said male or female subject.

The preferred P34 protein used has the sequence identified as SEQ ID NO:3 and the preferred antigenic fragment thereof includes, without limitation, MELFLAGRRVC (SEQ ID NO:4) OR CSQDYAEPNPTWQV (SEQ ID NO:5).

An immunocontraceptive vaccine for male or a female subject, which comprises an antigenic amount of P34 or an antigenic fragment thereof in association with a suitable pharmaceutically acceptable carrier, wherein said vaccine elicits an immunocontraception response by said male or female subject after its administration.

In accordance with the present invention there is provided a probe as a marker for male or female fertility, which comprises a cDNA sequence capable of hybridizing under stringent conditions with human acrosomal sperm protein P34.

In accordance with the present invention there is provided a method for the diagnosis of male or female infertility which comprises the steps of:

a) determining the amount of human P34 in a sperm or ovule sample; and b) comparing the determined amount of step a) with a fertile control sample.

The amount of human P34 in step a) may be determined using an antibody raised against human P34.

In accordance with the present invention there is provided a kit for the diagnosis of male or female infertility which comprises:

a) an anti-P34 antibody enzyme-labeled;

b) an enzyme substrate; and c) a fertile control sample.

A calibration curve for the amount of human P34 may be obtained using the fertile control sample of component (c) above.

For the purpose of the present invention the following terms are defined below.

The term "antigenic fragment" is intended to mean any fragment of said protein which is capable of eliciting an immune response pursuant to its administration to a subject.

BRIEF DESCRIPTION OF THE DRAWINGS

FIG. 1 illustrates the comparison of partial amino acid sequences with the corresponding amino acid sequence of P26h with AP27;

FIGS. 3A–3B illustrate the nucleotide sequence of the P26h cDNA;

FIG. 4 illustrates the alignment of the deduced amino acid sequence of P26h with the AP27 and the Carbonyl Reductase;

FIG. 8 illustrates the sequence homology of the human P34 (lower lane) counterpart of P26h (upper lane).

DETAILED DESCRIPTION OF THE INVENTION

Figure 2:
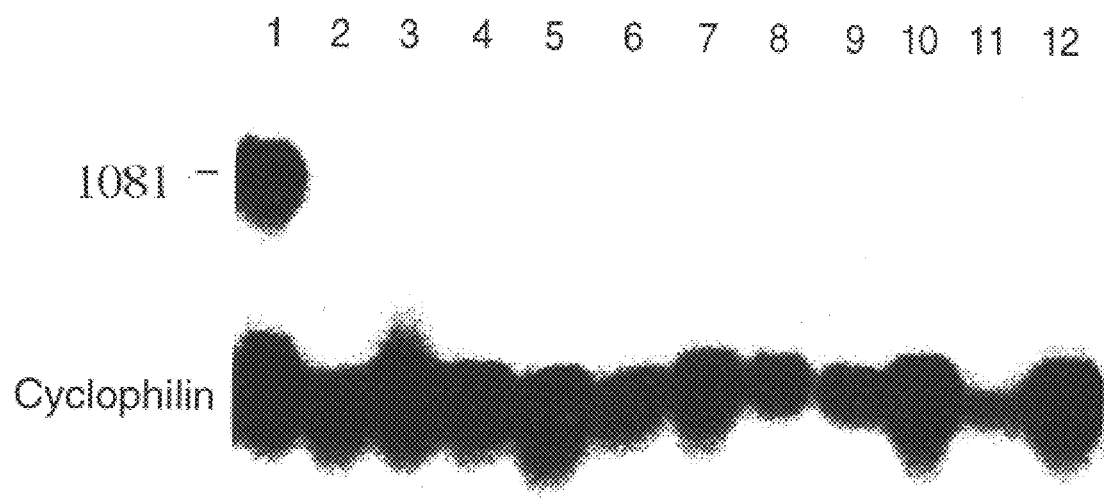
FIG. 2 illustrates a Northern blot analysis of hamster total RNA from 1) testis 2) whole epididymis 3) caput epididymis 4) corpus epididymis 5) cauda epididymis 6) Fat 7) Lung 8) heart 9) liver 10) kidney 11) muscle 12) brain probed with a nP26h 710 bp cDNA probe (upper panel) or with a positive Cyclophilin probe (lower panel)

During fertilization, mammalian spermatozoa must undergo a series of events in order to reach the oocyte surface and to perform syngamy. Some of these events occur during the epididymal transit where spermatozoa acquire their fertilizing ability. We have previously described a hamster sperm protein, P26h, acquired during the epididymal transit. P26h shows immunocontraceptive properties when used to actively immunize male.

In accordance with the present invention, we have undertaken the determination of the origin and of the sequencing of the encoding cDNA of this sperm protein showing male contraceptive properties. N-terminal sequencing of purified P26h and of peptides generated by partial proteolysis allowed partial identification of the protein. Northern blot analysis revealed that a major transcript encoding for P26h was localized the testicular MRNA whereas no signal was detectable in other somatic tissues of the hamster. A hamster testis cDNA library was screened and a P26h encoding cDNA was cloned and sequenced. The P26h cDNA sequence revealed a 85% identity with the cDNA corresponding to mouse Adipsin and of a Carbonyl Reductase. The deduced P26h amino acid sequence possesses specific domains of the Short Chain Dehydrogenase/Reductase (SDR) family proteins. Antibodies generated against synthetic peptides deduced from the cDNA sequence recognized the P26h on Western blots of detergent extracted hamster sperm proteins. On the other hand, in vitro translational products synthesized from the P26h cDNA were immunoprecipitated by a polyclonal antiserum produced against the purified hamster sperm P26h. In situ hybridization performed on tissues from the hamster reproductive tract, revealed that the P26h was principally transcribed in the seminiferous tubules and at a lower level in the corpus epididymidis. P26h shows unique features of the SDR family that can be used to induce contraception in males.

Materials and methods

Animals

Sexually mature Golden hamsters (*Mesocricetus auratus*; Charles River Inc., St. Constant, Qc, Canada) were used in this study. Hamsters were sacrificed under $CO_2$ atmosphere, the epididymidis were excised, defatted and dissected into caput, corpus and cauda segments. Tissues were frozen in liquid nitrogen and stored at −80° C. until use. Testicular and somatic tissues were proceeded the same way. For in situ hybridization fresh tissues were rinsed in PBS-DEPC (Phosphate buffered saline-Diethyl pyrocarbonate) and fixed at 4° C. for 2 h in 4% (w/v) paraformaldehyde freshly prepared in PBS. Tissues were cryoprotected by sequential incubations in 10% glycerol for 1 h at 4° C. under agitation and then overnight in 50% OCT. Tissues were embedded in OCT and frozen in liquid nitrogen. Cryosections of ~7 μm were collected on poly-L-Lysine coated slides, air-dried at −20° C., and stored at −80° C. until used.

N-chlorosuccinimide proteolysis

Proteins from cauda epididymal spermatozoa or from the epididymal fat pad were extracted with 0.5% Nonidet™ P40 (Sigma) as previously described and submitted to preparative SDS-PAGE. After Coomassie blue staining, the bands corresponding to a MW of 26 kDA were excised, washed twice with $H_2O$, and rinsed with a washing solution (50% (wt/vol) urea, 50% (vol/vol) ethanol). The polyacrylamide bands were incubated 30 min. in 20 mg/ml N-Chlorosuccinimide in washing solution, washed in water, and then incubated 3 times for 1 hour each, in an equilibrium solution (0.0625 M Tris-HCl pH 6.8, 20% (vol/vol) glycerol, 30% (vol/vol) B-mercaptoethanol, 6% (wt/vol) SDS). The band was loaded on a discontinuous polyacrylamide gel and submitted to electrophoresis. Patterns of proteins fragments were visualized by silver nitrate staining, or Western blotted using a P26h antiserum (Bérubé, B., Sullivan, R., 1994, *Biol. Reprod.*, 51: 1255–1263). Western blotted P26h fragments were also used for N-terminal sequencing as described below.

Partial amino acid sequence analysis

P26h was purified and absorbed on a piece of nitrocellulose sheet. One hundred μl of 50 mg/ml CNBr (Cyanogen Bromide) in 70% formic acid was added to 1 mg of the dry protein and incubated under nitrogen in the dark for 24 h. Digested peptides were loaded onto a VYDAK™ reversed-phase C18 column (250×1 mm) which was equilibrated with 0.1% (v/v) trifluoroacetic acid (TFA) in water and eluted with a 2–100% gradient of 0.08% (v/v) TFA in 80% acetonitrile. Fractions of 0.5 ml or smaller were collected at a flow rate of 50 μl/min. Protein sequence was performed on aliquots from one peak by automated Edman™ degradation with a pulsed-liquid phase sequencer.

RNA extraction

Tissues were homogenized with a Polytron™ in 1.5 ml of a fresh homogenization buffer solution (4 M guanidium thyocyanate, 25 mM sodium citrate pH 7, 0.5% sarcosyl, 0.1 M 2-mercaptoethanol). One ml of Cesium Chloride-homogenization buffer (2 g of CsCl/2,5 ml) was added to the tissue lysates. This was layered on cushion solution (5.7 M CsCl, 0.1 M EDTA, pH 7.5) and centrifuged at 60,000 g overnight. The RNA pellet was resuspended in TES solution (10 mM tris-HCl, 5 mM EDTA, 1% SDS, pH 7.4) and extracted with phenol/chloroform and chloroform/alcohol isoamyl 24:1. RNA was precipitated with 0.1 vol. of sodium acetate (3 M, pH 5.2) and 2.5 vol. of ethanol 95%. The RNA pellet were resuspended in DEPC water. The RNA quality was evaluated by electrophoresis on a 1% agarose gel. All solutions were made with DEPC water.

Northern blot analysis

Total RNA (20 μg) prepared from hamster and human tissues were electrophorized on 1% agarose-formaldehyde gels and transferred to a nylon membrane (Quiagen, Santa Clarita, Calif.) using 20× SSC (3 M NaCl, 0.3 M Na-Citrate). Air dried Northern blots were UV cross-linked and prehybridized at 42° C. for 4 h in 50% (vol/vol) formamide, 0.75 M NaCl, 0.05 M $NaH_2PO_4$, 0.005 M EDTA, 2× Denhardt's reagent [0.2% (wt/vol) Ficol 400, 0.2% (wt/vol) polyvinylpyrrolidone, 0.2% (wt/vol) BSA], 0.2 mg/ml herring sperm DNA (Sigma Chemicals, Mississauga, ON) and 0.1% SDS. The membrane was hybridized overnight at 42° C. in the same solution, to which [$\alpha$-$^{32}$P] dCTP-labeled DNA probes were added. The membranes were then washed twice in 0.1× SSC-0.1% SDS followed by a third wash of 30 min. at 65° C. in 0.1× SSC-0.1% SDS, and exposed on Kodak™ X-O-Mat film with intensifying screens for 6–18 h at −80° C. A RNA ladder (1.6–7.4 kb; Boehringer Mannheim, Laval, QC) was electrophoresed in parallel and Cyclophilin probe was used as a constitutive internal control.

RT-PCRs production of a P26h cDNA probe

The first amino acids sequence obtained (MKLNFSXLRLVTGAGKGIG) showed high homology with the peptide sequence of the Adipsin: a marker of adipocytes differentiation. From the nucleic acid sequence of the adipsin, two primers were selected according to OLIGO 4.01™ primer analysis software (National Biosciences, Plymouth, Minn.), chemically synthesized (sense downstream 5'-GTG ACA GGG GCA GGG AAA GGG-3' and antisense upstream 5'-GCA ACT GAG CAG ACT AGG AGG-3') and used for RT-PCR on the total RNA from hamster's testis.

Briefly, 5 μg of the total testis RNA were incubated with 0.5 μg oligo deoxythymidine primer at 70° C. for 10 min. in a final volume of 12 μl and then kept on ice. Samples were then incubated for 60 min. at 42° C. in a reaction mixture containing 4 μL of 5× buffer (250 mM Tris-HCl, 375 mM KCl, 15 mM $MgCl_2$), 10 mM dithiothreitol (DDT), 1.25 mM deoxynucleotide triphosphates (DNTP) and 200 U Super Script reverse transcriptase in a final volume of 20 μl. Expression of the P26h gene was determined by amplification of the cDNA. Each reaction contained 5 μl of RT template (or water as negative control), 1.5 mM $MgCl_2$, 1× buffer, 0.2 mM dNTPs, 10 μM of each primer and 1–5 U Taq polymerase (Pharmacia Biotech, Baie D'Urfé, QC) in a final volume of 50 μl. The PCR cycling conditions chosen were 1 min. at 95° C., 1 min. at 60° C., 1 min. at 72° C. for 30 cycles, followed by a 5 min. extension at 72° C. The reaction products were analyzed using electrophoresis on a 1% agarose gel; the bands were visualized by ethidium bromide staining.

The PCR band (~710 pb) was purified (Quiaquick; Quiagen), T-Cloned in pCR 3.5 (Invitrogen, San Diego, Calif.), and digested with EcoR1. The insert (710 bp) was separated from the vector and other fragments by electrophoresis on a 1% agarose gel, isolated from gel matrix with Na45 membrane (Schleicher & Schuell, Inc.), and random-prime labeled according to the supplier's instruction using the T7 Quick-Prime™ kit (Pharmacia Biotech, Baie D'Urfé, QC) with [$\alpha$-$^{32}$P] dCTP. Cyclophilin cDNA was also random-prime labeled using the same procedure.

Cloning and sequencing of P26h cDNA

Poly(A)$^+$RNA from hamster and human testicular tissues was purified from total RNA solution using a poly(A)$^+$RNA purification kit (Pharmacia Biotech, Baie D'Urfé, QC) according to the supplier's instructions. The cDNA library was prepared according to the instruction the of the supplier. Briefly, testicular poly(A)$^+$RNA was reverse-transcribed and ligated into the lambda Uni-Zap XR vector (Stratagene, La Jolla, Calif.). The lambda library was packaged and amplified using *Escherichia coli* XL1-Blue cells, and screened with the random-prime labeled 710 bp P26h cDNA. The positive clones were isolated by plaque purification and the longest one (1081 bp) was subcloned into pBluscript KS+. All nucleotide sequences were determined by the dideoxinucleotide termination method (Sanger) using T7 Sequenase v 2.0 kit. The labeled reaction products were analyzed on a DNA sequencer gel. Sequence translation was performed using Gene Jockey software (Biosoft, Cambridge, UK).

In situ hybridization

Tissues cryosections were fixed with freshly prepared 4% paraformaldehyde in PBS for 5 min at RT° (Room Temperature), incubated for 10 min. in 95% ethanol/5% acetic acid at −20° C., and rehydrated by successive baths of decreasing concentrations of ethanol diluted with DEPC-$H_2O$. Target RNA was unmasked by enzymatic digestion with 10 μg/ml proteinase K (Boehringer Mannheim) in PBS for 10 min. at 37° C., followed by a 5 min. incubation in 0.2% glycine. Sections were postfixed for 5 min with 4% paraformaldehyde in PBS, acetylated with 0.25% acetic anhydride, 0.1 M triethanolamine, pH 8.0, for 10 min., and finally washed with PBS.

Tissues were prehybridized for 1 h with a preheated 250 μg/ml salmon sperm DNA in a hybridization solution (0.3M NaCl, 0.01 M Tris-HCl pH 7.5, 1 mM EDTA, 1× Denhardt's solution, 5% dextran sulfate, 0.02% SDS and 50% formamide). Sections were then incubated overnight at 42° C., under coverslips, with 25 μl of heat-denatured antisense or sense CRNA probed with DIG (Digoxigenin: Boehringer Mannheim) according to supplier's instruction. Coverslips were removed, the sections were washed twice in 2× SSC at RT°, followed by two 10 min. washes at 42° C. in 2× SSC, 1× SSC and 0.2× SSC, respectively.

Hybridization reactions were detected by immunostaining with an alkaline phosphatase-conjugated anti-DIG antibobies. Nonspecific staining was blocked by incubation for 1 h with 5% (v/v) heat-inactivated sheep serum in 0.2 M Tris-HCl, 0.2 M NaCl, and 3% Tritons X-100. Sections were then incubated for 2 h at RT° with the alkaline phosphatase-conjugated anti-DIG antibodies diluted 1:1000 in blocking solution, washed with tris-HCl/NaCl buffer, and incubated with 0.1 M tris-HCl, pH 9.5, 0.1 M NaCl, and 0.01 M $MgCl_2$. The hybridization signal was visualized after a 10–15 min. incubation with the substrates nitroblue tetrazolium chloride and 5-bromo-4-chloro-3-indolylphosphate p-toluidine salt (GIBCO-BRL, Gaithersburg, Md.). Levamisole (2 mM; Sigma) was added to the reaction mixture to inhibit endogenous alkaline phosphatase. Slides were immersed in 1 mM EDTA, 0.01 Tris-HCl, pH 7.5, washed 5 min. in $H_2O$, counterstained with neutral red, dehydrated through baths of ethanol, cleared in xylene, and mounted with Permount (Fisher scientific, Nepean, Ontario, Canada).

Eukaryotic in vitro translation

In vitro translation was performed from circular plasmid DNA including the P26h cDNA. The TNT coupled reticulocyte lysate system was used according to the supplier's instructions (Promega, Madison, Wis., USA). Briefly, 0.5 μg of circular plasmid DNA was added directly to TNT rabbit reticulocyte lysate. $T_3$ RNA polymerase (Promega, Madison, Wis., USA) and $S^{35}$-methionine (10 mCi/ml) were added to the translation mixture. The reaction was performed for 2 hours at 30° C. The de novo synthesized proteins were analyzed by SDS-PAGE according to Laemmli. The gel was soaked in an enhancer solution (Amersham), dried, and exposed on X-Omat™ AR film (Kodak) for 6 hours at room temperature. In some experiments, the translational products were submitted to NCS proteolysis (as described above) before electrophoretic analysis.

In some experiments, the translational products were immunoprecipitated using an anti-P26h antiserum. 5 μl of the translation reaction mixtures were incubated 1 h at room temperature with the P26h antiserum (previously described Bérubé, B., Sullivan, R., 1994, *Biol. Reprod.*, 51: 1255–1263) or the control serum, both diluted in Tris-saline (50 mM Tris-HCl, 150 mM NaCl, pH 7.5). 50 μl of packed protein-A sepharose (Pharmacia) was added for 1 hour at room temperature. The immunoprecipitate was washed several times in tris-saline solution (50 mM Tris-HCl, 500 mM NaCl, pH 7.5). The immune complexes were dissociated in SDS-PAGE sample buffer (50 mM Tris-HCl pH 6.3, 2% SDS (w/v) and 5% (v/v) B-mercaptoethanol) and submitted to SDS-PAGE according to Laemmli. The gel was enhanced, dried, and exposed on X-Omat™ AR film (Kodak) for 12 hours at room temperature.

Results

When purified P26h was submitted to Edman degradation, 27 of the 29 amino acids generated were identified. A 17 kDa fragment obtained by NCS proteolysis of P26h allowed the identification of 15 of the 26 amino acids analyzed, whereas the fragment obtained following CNBr treatment allowed the identification of 8 of 9 additional amino acids. For a total of 40 amino acids identified by Edman degradation of P26h peptides, 37 showed homology with a mouse Adipsin sequence (FIG. 1). This protein has been shown to be a differentiation growth factor of mouse adipoblasts.

In the hamster, like many mammalian species, the epididymis is surrounded by a fat pad. In the mouse, an Adipsin mRNA is abundant in the epididymal fat cushion. We were concerned with the possibility that P26h N-terminal sequences obtained may result from a contamination of sperm protein preparation by epididymal fat pad originating Adipsin. A band corresponding to 26 kDa of an electrophoretic pattern of protein extracted from a large amount of epididymal fat cushion was excised and submitted to N-chlorosuccisinimide proteolysis (NCS). This digestion did not generate fragments on SDS-PAGE electrophoretic pattern whereas P26h NCS digest generated a 22.4 kDa fragment. Moreover, only the P26h and its NCS digested fragment were detected by a P26h antiserum used to probe a corresponding immunoblot. The NCS digested fragment of the P26h was sequenced and the inner sequence revealed also a high homology level with the Adipsin. The intact 26 kDa protein from the fat pad protein extract was submitted to the same procedure and no N-terminal sequence was obtained.

Figure 7:
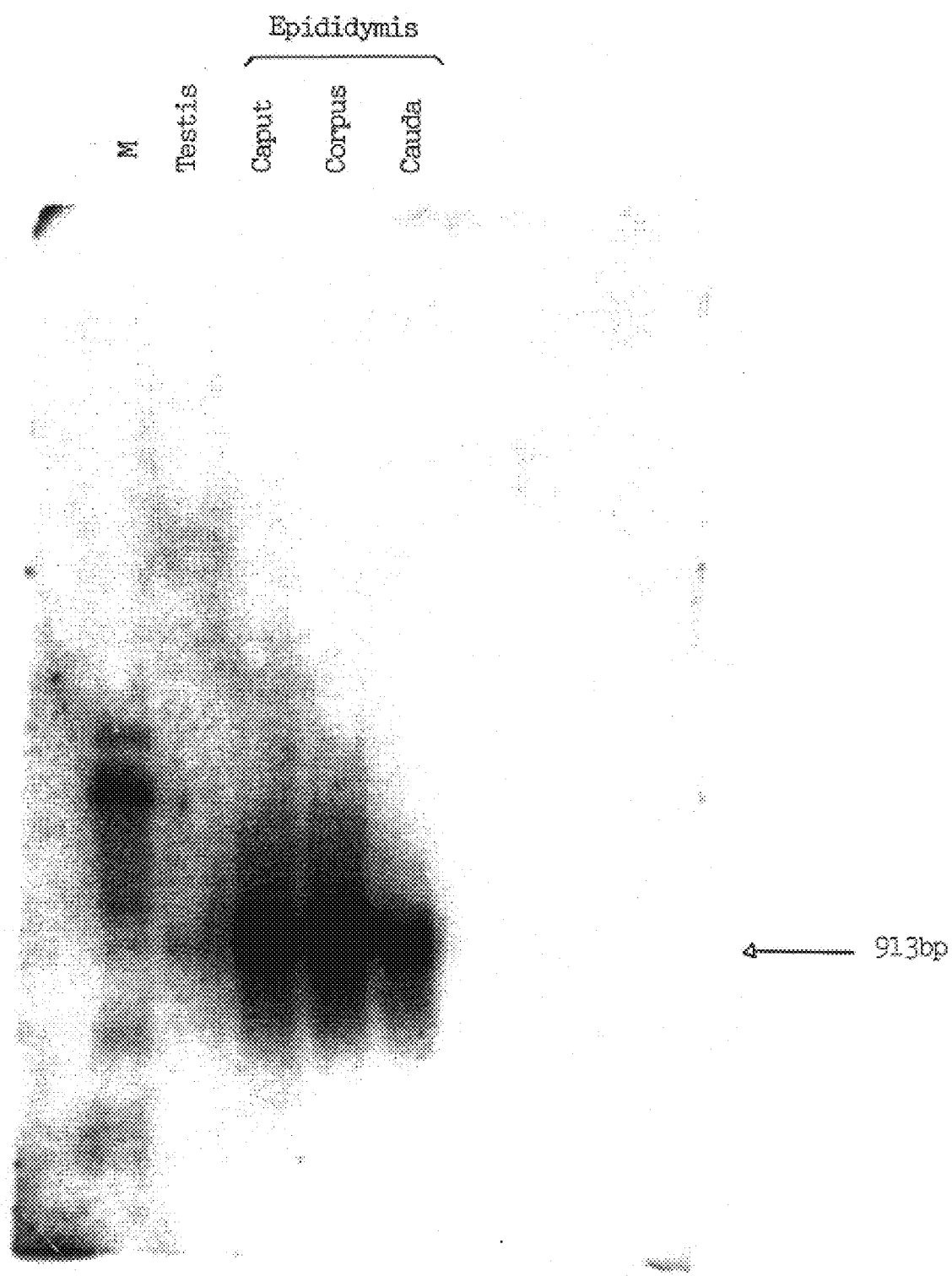
FIG. 7 illustrates a Northern blot analysis of human total RNA from 1) testis, 2) caput epididymidis, 4) corpus epididymidis, 5) cauda epididymidis, probed with a P34H cDNA probe.

RT-PCRs were performed with oligonucleotides derived from the cDNA sequence of the Adipsin. A 710 bp fragment was amplified from the hamster testis, cloned and sequenced. The sequence revealed that this fragment has 85% homology with the Adipsin cDNA. Using this fragment as a probe, we performed a Northern blot analysis to determine in which tissues P26h transcription occurs. Total RNA of several tissues were extracted and submitted to blot-hybridization analysis The Northern blots showed that the total P26h messenger RNA has 1081 bp and that it was transcribed exclusively in the testis. To confirm the presence of intact RNA in all samples, the same blot was probed with random cyclophilin DNA, and an intense signal was obtained in all samples (FIG. 2). By opposition, Northern blot analysis of mRNA prepared from human tissues revealed an abundant transcript in the epididymal tissues (FIG. 7).

A cDNA library was constructed in Lambda gtll from the hamster testicular MRNA and from the human epididymal tissues. $10^5$ clones of the primary library ($5\times10^5$ clones) were directly screened with the 710 pb cDNA probes. The first screening allowed the detection of 32 positive clones from which 11 were used for a second and third screening. The size of the inserts was determined by PCR and the longest insert (clone 2), was introduced in pBluescript SK(±) phagemid and sequenced. The P26h cDNA of 1081 bp has a 732 bp open reading frame, starting with a ATG codon at position 132 and a TAG stop codon at position 764, followed by a poly-adenylation signal, and a poly A tail (FIGS. 3A–3B). The sequence is numbered from the 5' end of the cDNA clone. The translation of the proposed open reading frame is shown below the nucleotide sequence and encodes a peptide of 244 amino acids terminating by a amber codon.

The deduced amino acid sequence predicted a 26 kDa MW protein which is in agreement with the molecular weight of the P26h as determined by SDS-PAGE. The N-terminal sequence of P26h and of its generated peptides determined by Edman degradation (FIG. 1) were also in agreement with the amino acid sequence deduced from the cDNA (FIG. 4). The P26h amino acid sequence was compared with the Adipsin and a carbonyl reductase, which showed a homology of 85% and 86% respectively. Adipsin and carbonyl reductase are members of the SDR (short side chain dehydrogenase/reductase) family proteins. The P26h also showed the conserved patterns of SDR, i.e. the NADH or NADPH coenzyme binding site and the active site which are respectively GlyXXXGlyXGly and TyrXXXLys (FIG. 4). The deduced amino acid sequence of the human homolog (FIG. 8, lower sequence) predicts a 244 amino acid peptide sharing the SDR characteristic with the hamster P26h (FIG. 8, upper sequence).

Expression of P26h mRNA is detected in the testis, using non-radioactive in situ hybridization. Digoxigenin-labeled anti-sense probe revealed the expression of the P26h MRNA in the adult hamster testicular seminiferous tubules. By opposition to the Northern Blot analysis, in situ hybridization revealed a weaker signal along the epididymis, principally in the corpus portion. Digoxigenin-labeled sense probe was used as a control for nonspecific hybridization.

Using the TNT™ coupled reticulocyte lysate system, we performed in vitro translation with circular plasmid including P26h cDNA. We detected a 26 kDa signal with total translation products on SDS-PAGE. (FIG. 6A3) Total translation products were then submitted to immunoprecipitation with anti-P26h antibody, which permitted the detection of a unique signal of 26 kDa on SDS-PAGE. (FIG. 6A2). Total translation products were further submitted to NCS proteolysis. The NCS proteolysis generates a 17 kDa fragment on SDS-PAGE in agreement with the deduced amino acids sequence and the previous NCS proteolysis of purified P26h.

Discussion:

During the epididymal transit, the mammalian spermatozoa acquire their fertilizing ability. One of the best documented physiological functions acquired by the spermatozoa during epididymal maturation is their ability to efficiently interact with the egg's zona pellucida. Our laboratory has been interested by these sperm surface modifications; mainly the addition of new surface proteins, or the post-translational modifications of preexisting sperm components, that are necessary to produce a functional male gamete. Using the hamster as a model, we have previously identified a sperm protein, P26h, which shows affinity for the homologous zona pellucida glycoproteins. P26h is abundant in the luminal fluid of the proximal region of the hamster epididymis, its concentration decreasing along the transit. Contemporarily, P26h accumulates on the spermatozoa during the epididymal maturation. P26h is exclusively located on the sperm surface covering the acrosomal cap of the mature spermatozoa; the subcellular domain involved in zona pellucida binding.

In accordance with the present invention, P26h has been purified following detergent extraction of cauda epididymal spermatozoa. This has been performed by preparative SDS-PAGE (Bérubé, B., Sullivan, R., 1994, *Biol. Reprod.*, 51: 1255–1263) as well as by chromatographic procedures. In the latter case, a single spot in two dimensional gel electrophoresis was obtained, this single protein being recognized by the anti-P26h on corresponding Western blot. These two preparations of purified P26h, as well as proteolytic fragments, have been N-terminal sequenced by Edman degradation. All the amino acid sequences obtained showed high homology with mouse Adipsin (FIG. 1). Adipsin has been described as a differentiation factor of adipoblasts in adipocytes. Adipsin mRNA has been shown to be present in high quantities in the mouse epididymal fat pad. In the hamster, as well as in the mouse, the majority of the epididymis is surrounded by a fat cushion. Considering that the purified P26h was obtained from spermatozoa recovered from the distal cauda epididymidis, we were concerned with the possibility that the N-terminal sequences were obtained from Adipsin liberated from adipocytes contaminating the sperm suspensions. This was conceivable if we considered that the Adipsin MW deduced from the mRNA sequence is of 27 kDa. Proteins from huge amounts of epididymal fat pad were extracted and proceeded in parallel with cauda epididymal spermatozoa. Protein bands of 26–27 kDa were excised from preparative SDS-PAGE of proteins extracted from fat pad adipocytes and from cauda epididymal spermatozoa. Intact 26–27 kDa bands and proteolytic fragments generated by NCS (N-Chlorosuccimide) digest were Western blotted and probed with the anti-P26h serum. The 26–27 kDa fat pad protein was undetectable by the anti-P26h antiserum (FIG. 2). Furthermore, the 26–27 kDa fat pad band and the P26h sperm protein were proceeded in parallel for N-terminal sequencing by Edman degradation. No signal was detectable when the fat pad protein was proceeded. From these results we can conclude that the N-terminal sequences obtained did not result from a contamination of sperm preparation by the epididymal fat pad.

Figure 5:
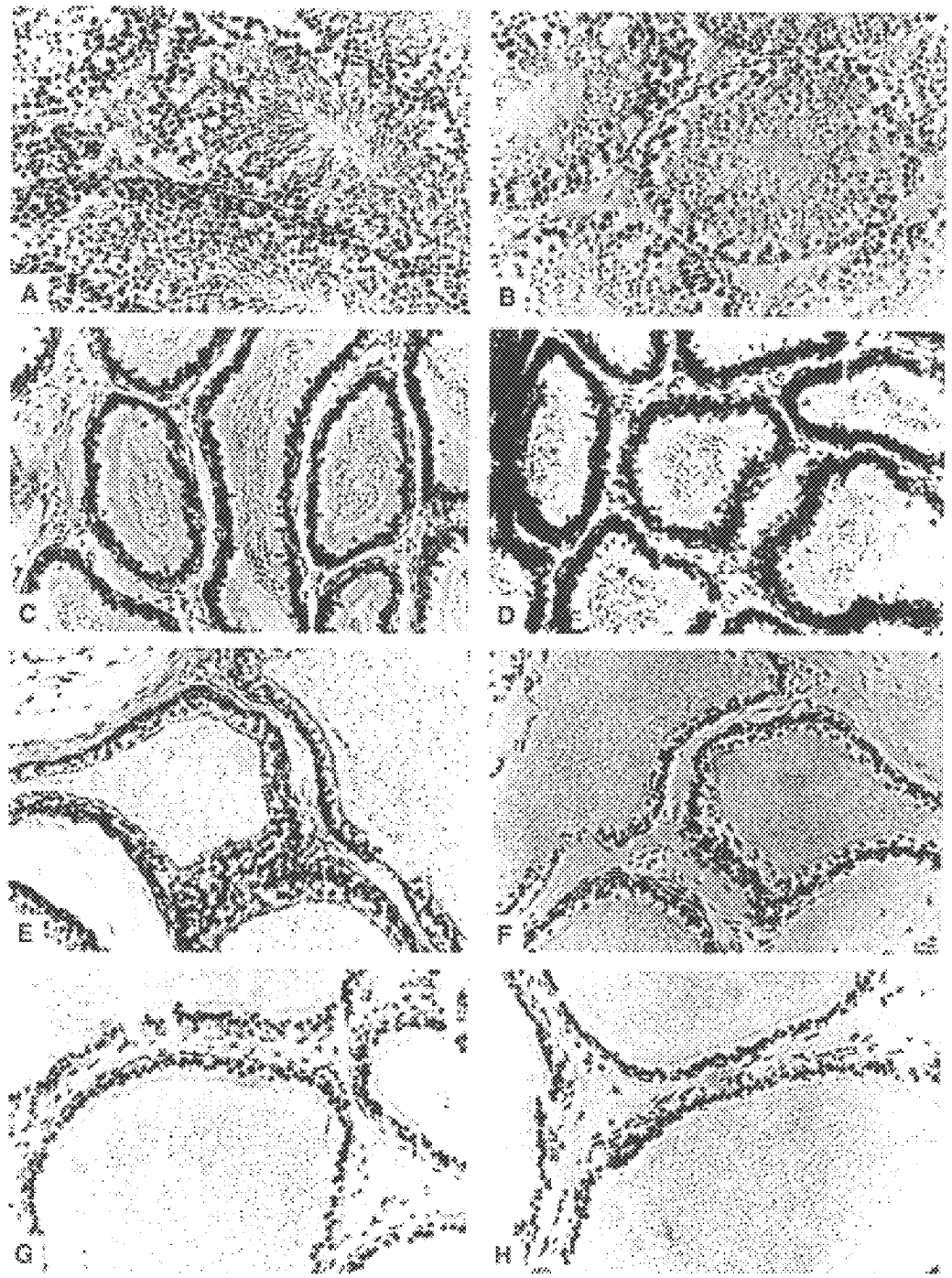
FIG. 5 illustrates in situ hybridization probed with the P26h RNAs probes.
Figure 6:
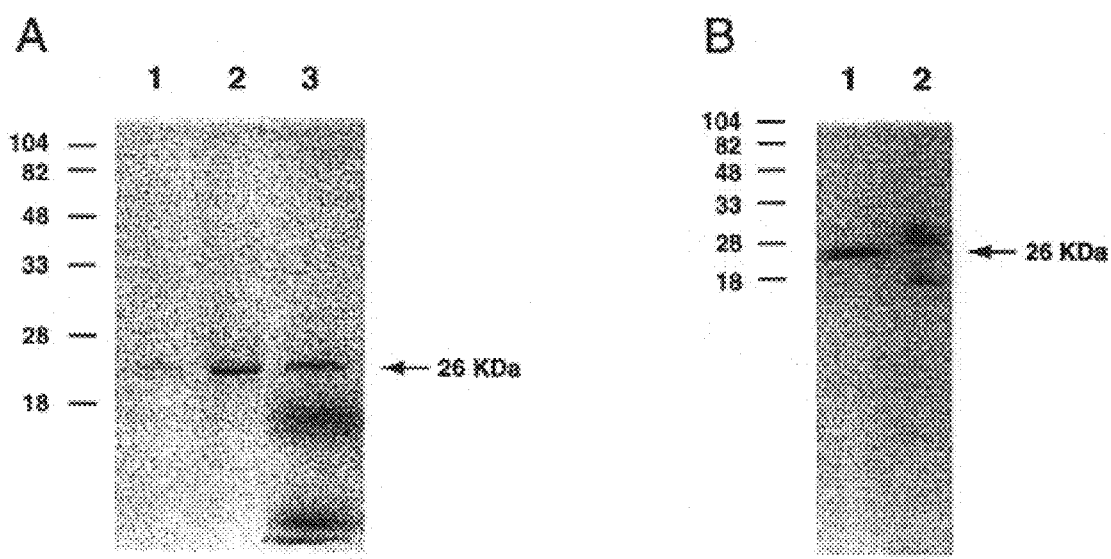
FIG. 6 illustrates the immunoprecipitation of P26h cDNA translational products.

Northern blot analysis revealed a major P26h transcript in testicular tissues of the sexually mature hamster (FIGS. 3A–3B). This mRNA is undetectable in the other tisssues analyzed, including the fat pad and the epididymis (FIGS. 3A–3B). This was unexpected since it was previously reported that an in vitro translational product encoded by mRNA of the proximal region of the epididymis can be immunoprecipitated by anti-P26h antibodies. In this study, in situ hybridization confirms that a P26h transcript is predominant in the testis and, at a lower level, in the epididymis. In situ hybridization has been performed with digoxigenin-labelled RNA probes system using an anti-digoxigenin antibody that allows amplification of the signal and provides a more sensitive mRNA detection than the traditional Northern blot analysis. A faint labelling is detectable all along the epididymis, a much stronger signal being associated with the corpus (FIG. 5). In many species, the corpus region is known to be a more active epididymal segment for protein synthesis and secretion. According to the Northern blot analysis (FIG. 2), P26h which is found at high concentration in the proximal region of the hamster epididymis probably originates from the testicular fluid as a secretion product of the seminiferous tubules, as suggested by the in situ localization of the transcript (FIG. 6). This protein may also be secreted by the corpus epididymidis. A dual testicular and epididymal origin has been described for other proteins interacting with the spermatozoa during epididymal maturation. Whether or not, the testicular and the epididymal P26h are identical or exist in different isoforms, as described for clusterin, remains to be determined.

The P26h being transcribed principally in testicular tissues (FIG. 2), a testicular cDNA was screened to clone the P26h cDNA. The longest transcript obtained from the library was sequenced and revealed a cDNA of 1081 bp coding for a 244 amino acids protein. The predicted MW of the translational product is in agreement with the electrophoretic behaviour of P26h extracted from cauda epididymal spermatozoa. The P26h cDNA shows high sequence homology with Adipsin, as expected from N-terminal amino acid sequences and with a carbonyl reductase known to be expressed in pig lung (FIG. 4). The sequence homology between P26h and these two proteins is 86% and 85% respectively. The deduced amino acid sequence also shows a high homology of 87% with the Adipsin and 80% with the Carbonyl Reductase. Considering that P26h is a sperm protein involved in gamete interactions, the biological function of these two proteins was puzzling. Adipsin has been described as a differentiation factor of adipoblast in adipocytes and its expression has been shown to be inhibited by activators of protein kinase C. The carbonyl reductase is a homotetramer that catalyzes the oxidation of secondary alcohols and aldehydes. This enzyme has been shown to be expressed specifically in the lung and mainly distributed in the mitochondria. Notwithstanding the high level of homology with Adipsin and a carbonyl reductase, P26h shows a complete different tissues distribution. P26h protein and its encoding MRNA are not expressed in the lung nor in the adipocyte (FIGS. 2, and Bérubé, B., Sullivan, R., 1994, *Biol. Reprod.,* 51: 1255–1263). Adipsin and carbonyl reductase are known to be members of the short-chain dehydrogenase/reductase (SDR) superfamily and P26h shows some of these properties.

The Short-Chain Dehydrogenase/Reductase superfamily (SDR) is formed by a variety of different proteins that exhibit residue identities of only 15–30%. This low level of sequence identity between the members indicates an early divergence. This is reflected by the wide range of functions fulfilled by the members of this superfamily. There are three classes of enzymes covering a wide range of EC numbers: 1, 4.2, 5.1, and 5.3, as well as members with unknown functions. Two consensus sequences are conserved in this family, the NAD(H) or NADP(H) binding domain, a N-terminal segment GlyXXXGLYXXGly, and the catalytic domain, a sequence TyrXXXLys. The P26h deduced amino acid sequence possesses these consensus domains as well as the Gly 129, Ser 136 and Pro 179 which are conserved in more than 90% of the SDR family members (FIG. 4).

Polyclonal antibodies have been produced against P26h and used to document the function of this sperm protein during the fertilization processes in the hamster. When added to an in vitro fertilization medium, the antibodies anti-P26h inhibits in a dose-dependent manner, the sperm-zona pellucida interaction. Furthermore, active immunization of male hamsters against the purified P26h results in an immune response associated with reversible infertility. Using the anti-P26h antiserum, a human counterpart of P26h has also been identified and was showed to be absent from sperm of men presenting with idiopathic infertility. In humans, this protein is also acquired by the spermatozoa during the epididymal transit. Taken together, these results clearly demonstrate the involvement of this sperm protein in the processes leading to fertilization. The P26h preparation that shows an immunocontraceptive properties is the same than the one used to determine N-terminal sequence by Edman degradation (FIG. 1). Furthermore, the polyclonal antiserum that allowed us to document the function of P26h in the processes of fertilization also reacts with the translational product encoded by the sequenced cDNA (FIG. 6). This clearly demonstrates that this SDR member is involved in mammalian sperm-egg interaction.

The mammalian spermatozoon is a highly polarized cell characterized by well defined membrane domains. Many sperm surface proteins have been proposed to play a role during the cascade of events occurring when the male gamete reaches the oocyte. Different sperm proteins have been proposed as candidates involved in zona pellucida binding. Some of them show enzymatic activity such as proacrosin, a trypsin like protease, a mannosidase, a galactosyltransferase, and P95: a hexokinase. The catalytic activity of these enzymes may not necessarily be involved in zona pellucida interaction, it is rather the substrate affinity that mediates this interaction. The biological function played by these proteins in gamete interactions is thus quite different from their enzymatic activity defined by their catalytic activity in cell metabolism. This discrepancy is reflected by their subcellular localization on the spermatozoon. To mediate zona pellucida recognition these enzymes must be localized at the sperm surface where they are classically known to be intracellular. This is well illustrated by the extracellular oriented sperm membrane mannosidase and galactosyltransferase, as well as by hexokinase which is at the surface of the mouse spermatozoa where it is known to be associated with the mitochondrial membrane. Like these potential zona pellucida ligand, P26h is localized at the hamster sperm surface, to the membrane domain covering the acrosome.

P26h belongs to the SDR superfamily characterized by highly different members with a low level of identity. This reflects distant duplications and early divergence. As a consequence, SDR family represents a great diversity in enzymatic activities and functions. An interesting example of an alternative function for an enzyme, is glyceraldehyde-3-phosphate dehydrogenase. This protein which is classically known as a glycolytic enzyme has been shown to act as a t-RNA binding protein with a function in cytoplasmic trafficking. SDR divergence is favourable for arising the of new functions; involvement in gamete interactions may be one of these. Considering that P26h has been previously shown to be involved in gamete interaction and to possess immunocontraceptive properties, cloning of a homologous cDNA in human allowed the identification of a human sperm protein with immunocontraceptive properties (FIG. 8). The blood-testis barrier is not present in the epididymis, allowing the neutralization of spermatozoa following immunization against an antigen involved in post-testicular maturation of the male gamete. The fact that the human sperm protein is specifically expressed in the epididymis (FIG. 7), strongly supports its potential as an immunocontraceptive target.

The present invention will be more readily understood by referring to the following example which is given to illustrate the invention rather than to limit its scope.

EXAMPLE I

Immiunocontraception vaccine

The human counterpart of the hamster cDNA P26h, encodes for an epididymal-specific protein that is important in sperm function. It will be possible to target this protein by specific antibodies using an immunocontraceptive approach. Men will be immunized with a peptide corresponding to the epididymal protein. This peptide will be chosen with regards to its antigenic properties. An immune response against that specific peptide will occur and no side effect is expected since the selected peptide shows high specificity for a sperm-epididymal protein. The antibodies will reach the spermatozoa within the excurrent duct (epididymis) since the blood-testis barrier is not present at the level of the epididymis. The antibodies will neutralize the fertilizing ability of the spermatozoa as already shown with the hamster P26h and will confer an immuncontraceptive protection.

The peptide will be coupled to a carrier that will modulate the half-life of the circulating peptide. This will allow the control on the period of contraceptive protection. The peptide-carrier will be emulsified in an adjuvant and administrated by usual immunization route.

In men under such an immunocontraceptive regimen, the circulating titer of anti-peptide antibodies will be an indication of the contraceptive efficiency. Expected reversibility will be predicted by standard immunological determination of the titer of antibodies specific to the specific peptide.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method of immunocontraception of a male or female subject, which comprises administering to said male or female subject an antigenic fragment of a P34 protein to elicit an immunocontraception response by said male or female subject.

2. The method of claim 1, wherein said P34 protein is encoded by the sequence as set forth in SEQ ID NO:3, and wherein said antigenic, fragment has an amino acid sequence selected from the group consisting of SEQ ID NO:4 and SEQ ID NO:5.

3. An immunocontraceptive vaccine for a male or female subject, which comprises an antigenic fragment of a P34 protein in association with a suitable pharmaceutically acceptable carrier, wherein said vaccine elicits an immunocontraception response by said male or female subject after its administration.

* * * * *